United States Patent
DiFoggio et al.

(10) Patent No.: US 9,441,480 B2
(45) Date of Patent: Sep. 13, 2016

(54) WAVELENGTH-SELECTIVE, HIGH TEMPERATURE, NEAR INFRARED PHOTODETECTORS FOR DOWNHOLE APPLICATIONS

(71) Applicants: Rocco DiFoggio, Houston, TX (US); Sebastian Csutak, Houston, TX (US)

(72) Inventors: Rocco DiFoggio, Houston, TX (US); Sebastian Csutak, Houston, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 408 days.

(21) Appl. No.: 14/045,423

(22) Filed: Oct. 3, 2013

(65) Prior Publication Data

US 2015/0096746 A1    Apr. 9, 2015

(51) Int. Cl.
| | | |
|---|---|---|
| *G01V 13/00* | (2006.01) | |
| *E21B 49/08* | (2006.01) | |
| *G01J 3/10* | (2006.01) | |
| *G01J 3/36* | (2006.01) | |

(52) U.S. Cl.
CPC ............. *E21B 49/081* (2013.01); *G01J 3/10* (2013.01); *G01J 3/36* (2013.01); *E21B 2049/085* (2013.01)

(58) Field of Classification Search
CPC ............................. G01J 3/2506; G01J 3/10
USPC ........................................................ 250/262
See application file for complete search history.

(56) References Cited

U.S. PATENT DOCUMENTS

| | | |
|---|---|---|
| 6,803,581 B2 | 10/2004 | Prince et al. |
| 7,423,258 B2 | 9/2008 | DiFoggio et al. |
| 7,598,485 B2 | 10/2009 | Csutak |
| 7,638,761 B2 | 12/2009 | Csutak |
| 7,707,883 B2 | 5/2010 | DiFoggio |
| 7,763,845 B2 | 7/2010 | Estes et al. |
| 7,778,296 B1 | 8/2010 | Vuckovic et al. |
| 7,847,253 B2 | 12/2010 | Carey et al. |
| 7,884,439 B2 | 2/2011 | Mazur et al. |

(Continued)

FOREIGN PATENT DOCUMENTS

| | | |
|---|---|---|
| WO | WO02056430 A2 | 7/2002 |
| WO | WO2009023523 A1 | 2/2009 |

OTHER PUBLICATIONS

Tanabe et al. "All-silicon sub-Gb/s telecom detector with low dark current and high quantum efficiency on chip", Appl. Lett. 2010, vol. 96, p. 101103.*

(Continued)

*Primary Examiner* — David Porta
*Assistant Examiner* — Meenakshi Sahu
(74) *Attorney, Agent, or Firm* — Cantor Colburn LLP

(57) ABSTRACT

An apparatus for estimating a property of a downhole fluid includes a carrier configured to be conveyed through a borehole penetrating the earth, a fluid extraction device disposed at the carrier and configured to extract a sample of the downhole fluid, and a probe cell having a window to receive the sample. The apparatus further includes a light source to illuminate the sample through the window with light photons, and a photodetector to receive light photons through the window that have interacted with the downhole fluid and generate a signal indicative of an amount of the received light photons. The generated signal is indicative of the property. The photodetector has an optical cavity having a semiconductor that has a difference between a valence energy band and a conduction energy band for electrons that is greater than the energy of each of the received light photons.

21 Claims, 5 Drawing Sheets

(56) References Cited

U.S. PATENT DOCUMENTS

| | | | |
|---|---|---|---|
| 7,886,821 | B2 | 2/2011 | DiFoggio |
| 7,902,545 | B2 | 3/2011 | Csutak |
| 7,907,277 | B2 | 3/2011 | Csutak |
| 7,968,841 | B2 | 6/2011 | Csutak |
| 8,039,792 | B2 | 10/2011 | Nikitin et al. |
| 8,068,226 | B2 | 11/2011 | Csutak |
| 8,304,714 | B2 | 11/2012 | Csutak |
| 2005/0007583 | A1 | 1/2005 | DiFoggio |
| 2008/0073744 | A1 | 3/2008 | Masini et al. |
| 2009/0114805 | A1 | 5/2009 | Csutak |
| 2009/0237666 | A1 | 9/2009 | Vollmer et al. |
| 2009/0284259 | A1 | 11/2009 | Csutak |
| 2010/0018703 | A1 | 1/2010 | Lovell et al. |
| 2010/0231905 | A1 | 9/2010 | Christian et al. |
| 2010/0282321 | A1 | 11/2010 | Fenollosa Esteve et al. |
| 2011/0277540 | A1 | 11/2011 | Ioppolo et al. |
| 2012/0161269 | A1 | 6/2012 | Aumont et al. |
| 2013/0062514 | A1* | 3/2013 | Csutak ............... G01J 3/0256 250/262 |
| 2013/0175438 | A9 | 7/2013 | Ford et al. |

OTHER PUBLICATIONS

Notification of Transmittal of the International Search Report and the Written Opinion of the International Searching Authority; PCT/US2014/058992; Korean Intellectual Property Office; Mailed Jan. 26, 2015; 17 pages.

Hayakawa, et al., "Two-photon-absorption photodiodes in SI photonic-crystal slow-light waveguides", Appl. Phys. Lett., 102, 031114 (2013); doi: 10.1063/1.4789393, 4 pages. http://dx.doi.org/10.1063/1.4789393.

Pearl, et al., "Three photon absorption in silicon for 2300-3300 nm", Applied Physics Letters 93, 131102 (2008), 6 pages.

Casalino, "Near-Infrared Sub-Bandgap All-Silicon Photodetectors: A Review", International Journal of Optics and Applications, 2012, 2(1):pp. 1-16, Doi: 10.5923/j.optics.20120201.01, http://journal.sapub.org.optics.

Casalino et al., Near-Infrared Sub-Bandgap All-Silicon Photodetectors: State of the Art and Perspectives, ISSN 1424-8220, Sensors 2010, 10, pp. 10571-10600, www.mdpi.com/journal/sensors.

Venkatram et al., "Size dependent multiphoton absorption and refreactino of CdSe nanoparticles", Sep. 17, 2007 / vol. 15, No. 19 / Optics Express 12258, 6 pages.

Tanabe, Sumikura, Taniyama, Shinya, Notomi, All-silicon sub-Gb/s telecom detector with lowdark current and high quantum efficiency on chip, NTT Basic Research Laboratories, Japan, Applied Physics Letters, vol. 96, No. 10, Mar. 2010, 3 pages.

Zheng, Charbei, Kwok, "Mircoporous Silicon as a Light Trapping Layer for Photodiodes", The Electrochemical Society, Electrochemical and Solid-State Letters, 3 (7), 2000, pp. 338-339.

* cited by examiner

WAVELENGTH-SELECTIVE, HIGH TEMPERATURE, NEAR INFRARED PHOTODETECTORS FOR DOWNHOLE APPLICATIONS

BACKGROUND

Geologic formations are used for many applications such as hydrocarbon production, geothermal production, and carbon dioxide sequestration. Typically, boreholes are drilled into the formations to provide access to them. Various downhole tools may be conveyed in the boreholes in order to characterize the formations. Characterization of the formations and the fluids within provides valuable information related to the intended use of the formation so that drilling and production resources can be used efficiently.

Several types of downhole tools use a semiconductor photodetector to detect and measure an amount of photons for various characterization processes such as spectroscopy for sample identification or chemical analysis. However, borehole temperatures can be very high, up to 200° C. or more, and degrade the performance of these photodetectors especially for detecting photons in the near-infrared range of wavelengths. Hence, improvements in semiconductor photodetectors that are required to operate accurately at high downhole temperatures would be well received in the drilling and geophysical exploration industries.

BRIEF SUMMARY

Disclosed is an apparatus for estimating a property of a downhole fluid. The apparatus includes: a carrier configured to be conveyed through a borehole penetrating the earth; a fluid extraction device disposed at the carrier and configured to extract a sample of the downhole fluid; a probe cell having a window and configured to receive the sample; a light source configured to illuminate the sample through the window with light photons; and a photodetector disposed at the carrier and configured to receive light photons through the window that have interacted with the downhole fluid and generate a signal indicative of an amount of the received light photons, wherein the photodetector includes an optical cavity having a semiconductor that has a difference between a valence energy band and a conduction energy band for electrons that is greater than the energy of each of the received light photons; wherein the signal is indicative of the property.

Also disclosed is a method for estimating a property of a downhole fluid. The method includes: conveying a carrier through a borehole penetrating the earth; extracting a sample of the downhole fluid using a fluid extraction device disposed at the carrier; depositing the sample in a probe cell having a window; illuminating the sample through the window with light photons using a light source disposed at the carrier; receiving light photons through the window that have interacted with the downhole fluid and generating a signal indicative of an amount of the received light photons using a photodetector disposed at the carrier, the photodetector having an optical cavity that has a semiconductor having a difference between a valence energy band and a conduction energy band for electrons that is greater than the energy of each of the received light photons; and estimating the property using a processor that receives the signal.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method presented herein by way of exemplification and not limitation with reference to the figures.

Disclosed are apparatus and method estimating a property of a downhole fluid. The fluid may be a borehole fluid or a formation fluid. A "downhole fluid" as used herein includes any gas, liquid, flowable solid and other materials having a fluid property. A downhole fluid may be natural or man-made and may be transported downhole or may be recovered from a downhole location. Non-limiting examples of downhole fluids include drilling fluids, return fluids, formation fluids, production fluids containing one or more hydrocarbons, oils and solvents used in conjunction with downhole tools, water, brine, and combinations thereof. The apparatus and method involve extracting a sample of the fluid using a fluid extraction device conveyed through a borehole that may contain the fluid or provide access to a formation containing the fluid. The sample is illuminated by a light source and light, which has interacted with the sample and possesses a characteristic that corresponds to a property of interest, is detected by a combined optical cavity and associated photodiode (or other quantum photodetector, such as a phototransistor), which has a much wider band gap than would be permissible to detect near-infrared light if there was only the usual single-photon absorption process. This wider band gap minimizes any thermal promotion of electrons form the valence band to the conduction band that can occur at high downhole temperatures. The photodetector is a semiconductor device using two-photon absorption in order to provide enough energy to elevate electrons from the valence band to the conduction band to provide an electrical current indicative of the amount of photons that are detected. Without the two-photon absorption attribute and using a narrower energy band gap photodiode that is normally used to detect near infrared light, the high temperature in the borehole, which can be as high as 200° C., would provide enough energy alone to electrons to cause a signal current to flow without detection of photons. This current may be referred to as "dark current" because the current occurs in the absence of light. The low probability of two-photon absorption occurring becomes many times more likely when the light is bouncing or reflecting back and forth in a resonant optical cavity as in this invention. Roughly speaking, if the resonant optical cavity has a Q-factor of 100,000, then the probability of two-photon absorption occurring is increased by a factor of 100,000.

Figure 1:
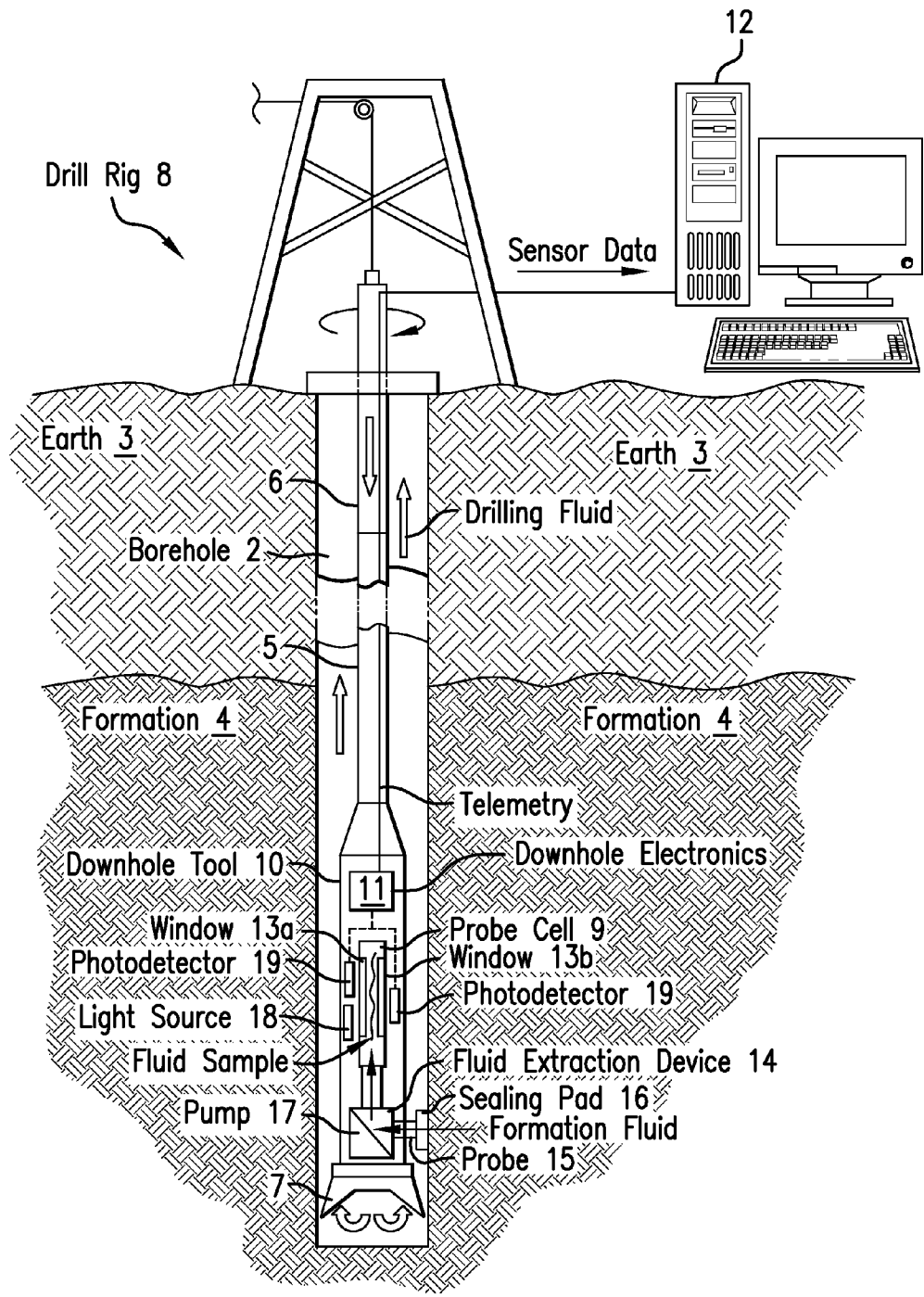
FIG. 1 illustrates a cross-sectional view of an exemplary embodiment of a downhole tool disposed in a borehole penetrating the earth.

FIG. 1 illustrates a cross-sectional view of an exemplary embodiment of a downhole tool 10 disposed in a borehole 2 penetrating the earth 3, which may include an earth formation 4 containing a formation fluid. The downhole tool 10 is configured to perform tests or measurements on a sample of the formation fluid in order estimate a property of the fluid. In a non-limiting embodiment, the downhole tool 10 may be configured as a spectrometer to estimate a chemical composition of the formation fluid.

The downhole tool 10 is conveyed through the borehole 2 by a carrier 5, which can be a drill tubular such as a drill string 6. A drill bit 7 is disposed at the distal end of the drill string 6. A drill rig 8 is configured to conduct drilling operations such as rotating the drill string 6 and thus the drill bit 7 in order to drill the borehole 2. In addition, the drill rig 8 is configured to pump drilling fluid through the drill string 6 in order to lubricate the drill bit 7 and flush cuttings from the borehole 2. Downhole electronics 11 are configured to operate the downhole tool 10, process measurement data obtained downhole, and/or act as an interface with telemetry to communicate data or commands between downhole components and a computer processing system 12 disposed at the surface of the earth 3. Non-limiting embodiments of the telemetry include pulsed-mud and wired drill pipe for real time communications. System operation and data processing operations may be performed by the downhole electronics 11, the computer processing system 12, or a combination thereof. The downhole tool 10 may be operated continuously or at discrete selected depths in the borehole 2. In an alternative embodiment, the carrier 5 may be an armored wireline, which may also provide communications with the surface processing system 12.

In the embodiment of FIG. 1, the downhole tool 10 includes a fluid extraction device 14. The fluid extraction device 14 includes an extendable probe 15 configured to extend from the tool 10 and seal to a wall of the borehole 2 using a sealing pad 16. Pressure is reduced inside the probe 15 using a pump 17 to draw a sample of formation fluid into the device 14 and then depositing it into a probe cell 9 where the sample can be analyzed. The probe cell 9 includes a window 13 through which light photons may be used to analyze the sample. The fluid extraction device 14 may also be configured to extract a sample of a fluid of interest from the borehole directly without the probe 15 extending. Other components (not shown) may be used to flush the sample from the probe cell and clean the probe cell before another sample is deposited in that probe cell.

The downhole tool 10 in FIG. 1 includes a light source 18 configured to illuminate the sample in the probe cell 9 through the window 13. The light source 18 is selected to emit light in a high temperature downhole environment. In one or more embodiments, the light source 18 emits light over a wide band of wavelengths and in one example is a tungsten bulb where the filament temperature can reach 3000° K. Non-limiting embodiments of the light source 18 for probing hydrocarbon molecules include InSb optical sources and quantum cascade lasers or light emitting diodes (LEDs). The light photons illuminating the sample interact with the molecules of the sample to modify a characteristic of the illuminating light. The modified light is received by a photodetector 19 either through the window 13a for reflective spectroscopy or through another window 13b for transmissive spectroscopy. The photodetector 19 is configured to detect photons of the modified light in the high temperature downhole environment without producing any or significant dark current that would affect the accuracy of photon detection for estimating the property of interest.

Figure 2:
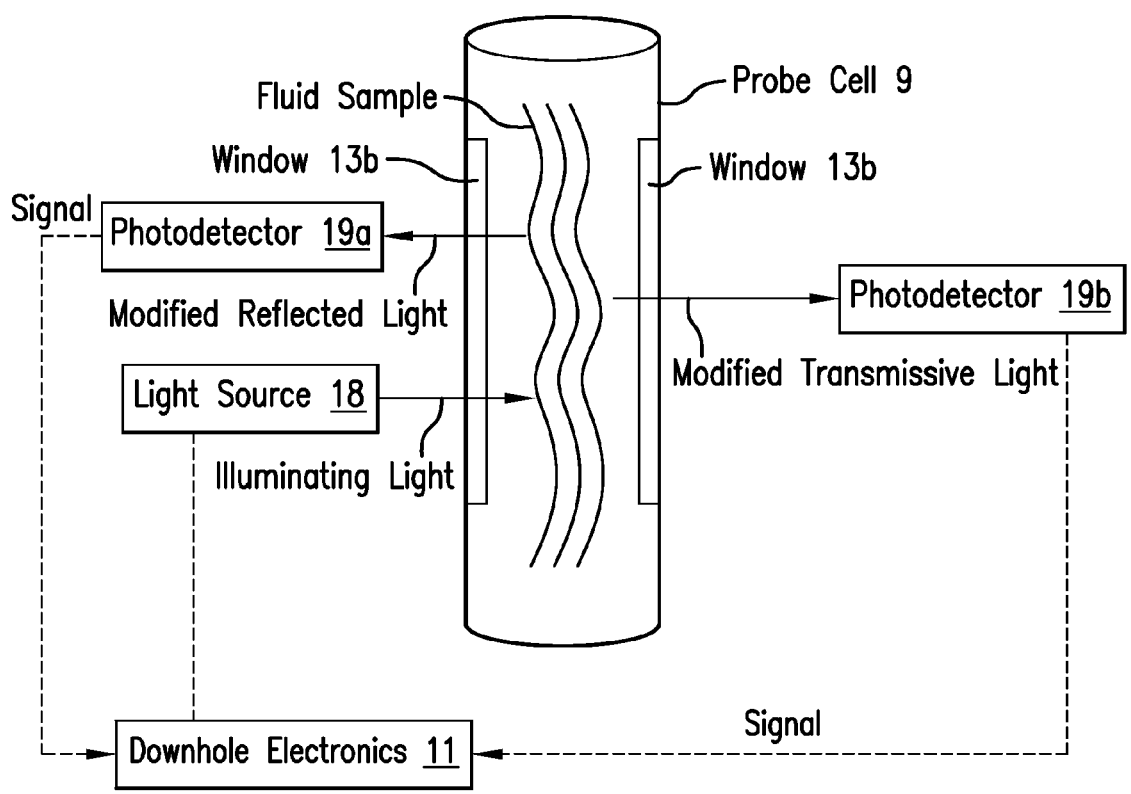
FIG. 2 depicts aspects of the downhole tool configured as a spectrometer.

FIG. 2 depicts aspects of the downhole tool 10 configured as a spectrometer. The photodetector 19 is coupled to a data processor such as the downhole electronics 11 or the computer processing system 12 for receiving and processing a signal from the photodetector 19 in order to estimate the property. The photodetector 19 produces a signal that contains information related to an amount of photons detected. In one or more embodiments, the data processor determines at which wavelength or wavelengths the received modified light has peaks of light intensity and matches or compares those wavelengths to a reference such as a lookup table, which may correlate a chemical identity or composition to certain light wavelengths having peak intensities. In this manner, the chemical identity or composition or the sample may be determined. In FIG. 2, photodetector 19a is configured for reflective spectroscopy while photodetector 19b is configured for transmissive spectroscopy.

Figure 3:
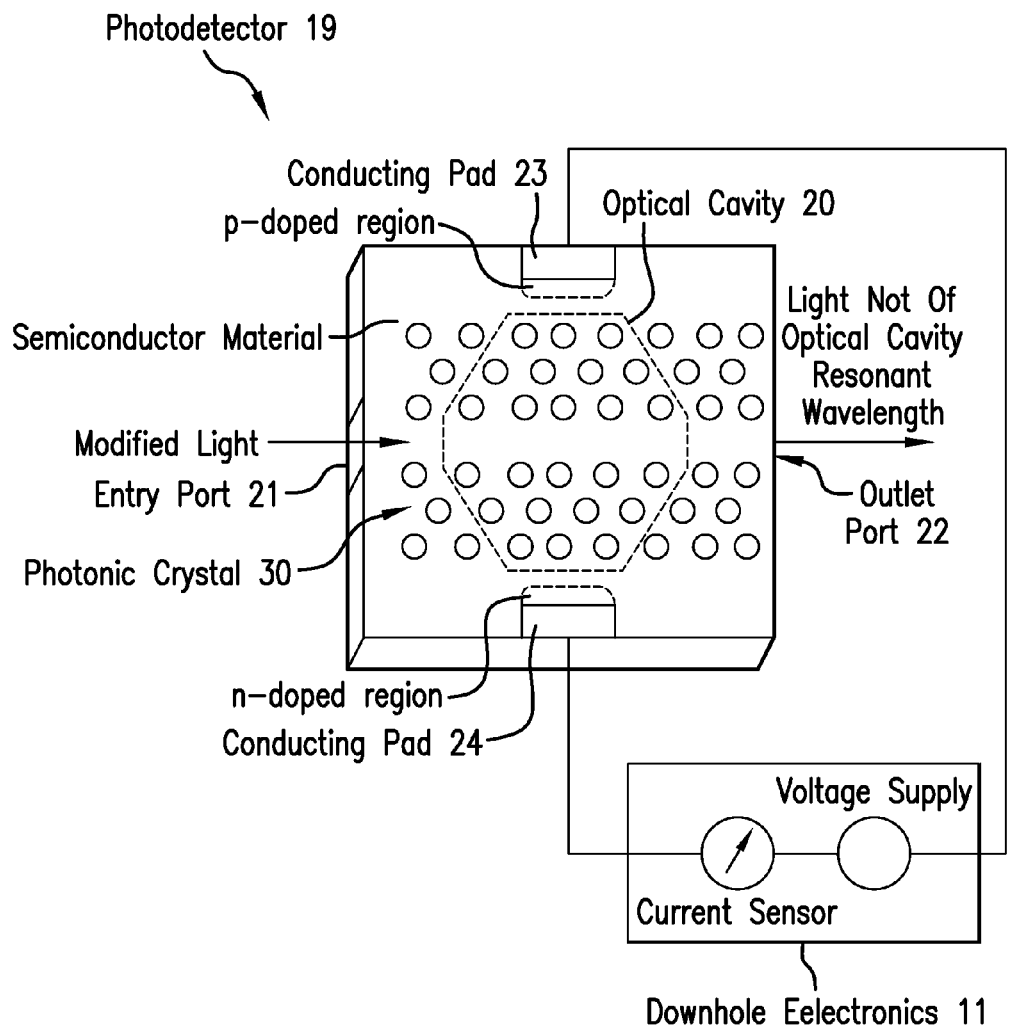
FIG. 3 depicts aspects of a photodetector configured for near-infrared spectroscopy.

FIG. 3 depicts aspects of the photodetector 19 configured for near-infrared spectroscopy, which detects photons in the wavelength range of from about 800 nm to 2500 nm, in a top-view. Near-infrared spectroscopy poses significant challenges for prior art quantum photodetectors in a downhole environment due to the temperature downhole being high enough to provide individual electrons with enough energy by temperature alone to be elevated from a valence energy band into a conduction energy band where the elevated electrons conduct electrical current to produce dark current. In contrast, the photodetector 19 includes a semiconductor material where the energy bandgap is sufficiently wide enough to prevent or significantly reduce dark current. However, this wide bandgap prevents individual electrons from being elevated into the energy conduction band by receiving one photon's worth of energy in the near-infrared range during a photon-electron interaction that transfers energy from the photon to the electron. In order to provide individual electrons with enough energy to be elevated into the energy conduction band, the photodetector 19 employs a physical phenomenon referred to as two-electron absorption (TPA). In TPA, two photons of identical or different wavelengths are simultaneously or near simultaneously absorbed by one electron to impart the combined energy of the two photons to that electron. In the photodetector 19, the semiconductor material is selected such that the energy bandgap is wide enough to prevent or significantly reduce dark current while being narrow enough such that the energy of two photons is sufficient to elevate one electron across the bandgap and into the conduction band. In one or more embodiments, silicon is selected as the semiconductor material.

The probability of TPA occurring is much less than the probability of one electron absorbing a single photon. Hence, in order to increase the probability of TPA occurring, the photodetector 19 includes an optical cavity 20 made into the semiconductor material. The optical cavity 20 is configured to have a high Q, which may be on the order of 100,000 as a non-limiting example. Photons of a resonant wavelength that enter the optical cavity 20 by the entry port 21 resonate (i.e., reflect back and forth many times) in the optical cavity 20 and do not exit. By resonating in the optical cavity 20, those photons increase the probability of TPA occurring with electrons in the energy valence band and, thereby, traverse the energy bandgap into the energy conduction band. Photons that are not of the resonant wavelength exit the optical cavity 20 via the outlet port 22. In one or more embodiments, the optical cavity 20 is a photonic crystal. The photonic crystal has regularly repeating regions of a high dielectric constant, such as the crystal material, and a low dielectric constant, such as holes. For example, the photonic crystal may have a plurality of holes, the dimensions and locations of which are configured to tune the photonic crystal to a particular resonant wavelength. The mismatch between the high index of refraction of the semiconductor material and the relatively lower index of refraction of the holes (e.g., the holes contain air, which is less dense than the semiconductor material and thus has a lower index of refraction) provides one or more modes of light that resonate in the photonic crystal. The photonic crystal is not limited to having holes as the lower refractive index region, but can include any material placed in a regular periodic pattern that has a lower refractive index than that of the semiconductor crystal. In that photonic crystals are known in the art, they are not discussed in further detail.

Still referring to FIG. 3, a first conducting pad 23 and a second conducting pad 24 are coupled to the optical cavity 20, which is a photonic crystal 30. Regions of the crystal around each of the conducting pads may be appropriately doped to form a PIN junction with the optical cavity of the photonic crystal placed between p and n doping areas. The conducting pads 23 and 24 form a circuit with a voltage supply 25 to bias the PIN junction and a current sensor 26 to measure current induced by TPA. The voltage supply 25 and/or the current sensor 26 may be included in the downhole electronics 11. It can be appreciated that in embodiments that require an absolute measure of the number of photons detected, the sensed current may have to be scaled knowing that it takes two photons to elevate one electron into the conduction energy band.

Figure 4:
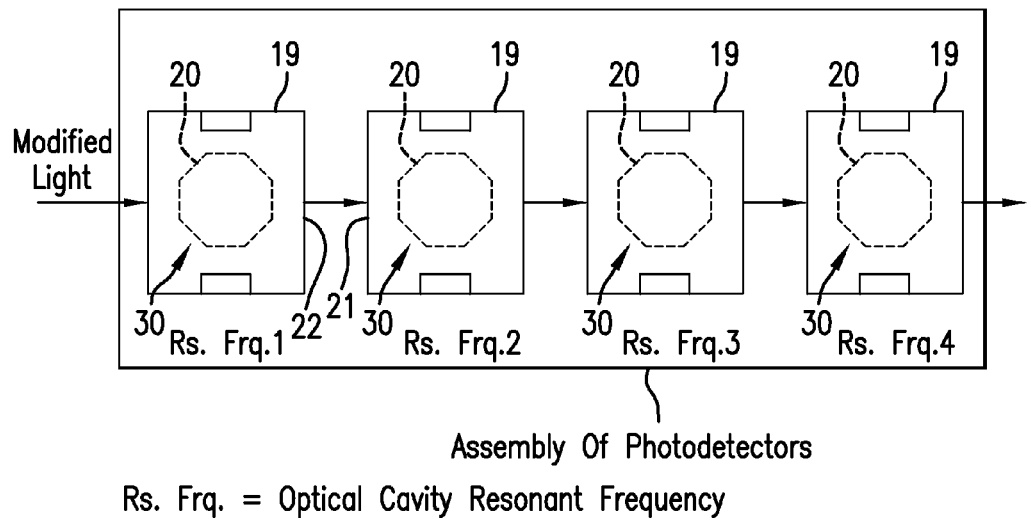
FIG. 4 depicts aspects of a plurality of photodetectors configured for spectroscopy.
Figure 5:
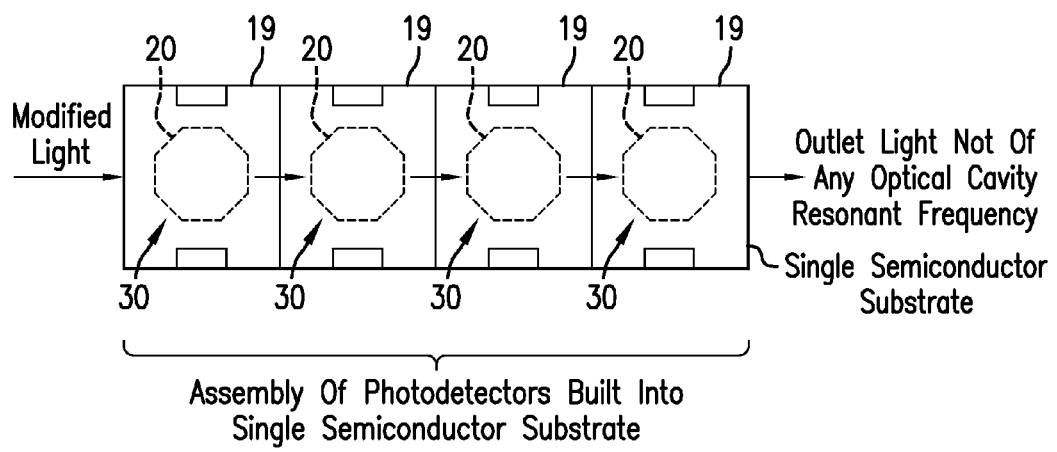
FIG. 5 depicts aspects of a plurality of photodetectors fabricated into a single semiconductor crystal.

Because the optical cavity 20 can be produced to have a single resonant wavelength, an optical filter is not required to filter incoming photons in applications where it is desired to have the photodetector 19 be sensitive to one particular wavelength of incoming light photons. Hence, in one or more embodiments of a spectroscopy application, the downhole tool 10 may include a plurality of photodetectors 9 as illustrated in FIG. 4 where each photodetector 19 in the plurality has a photonic crystal that is tuned to a unique resonant wavelength. Each resonant wavelength is generally tuned to a wavelength that corresponds to a property or chemical composition of interest. In one or more embodiments, the plurality of photodetectors 9 is configured such that the outlet port of one photodetector 9 leads into the inlet port of an adjacent photodetector 9 as illustrated in FIG. 4. In one or more embodiments, the plurality of photodetectors 9 is fabricated into a single semiconductor substrate as illustrated in FIG. 5.

Figure 6:
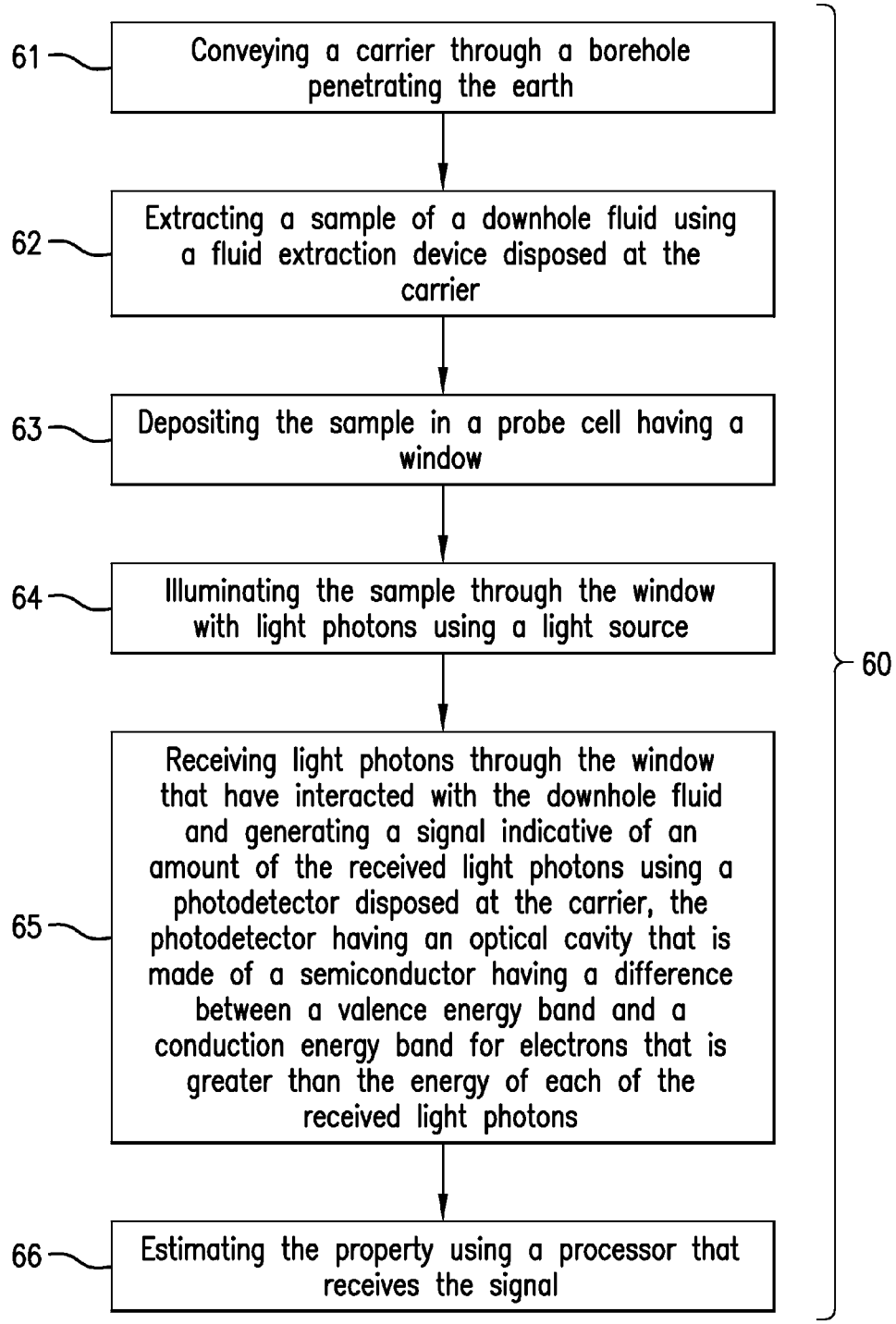
FIG. 6 is a flow chart of a method for estimating a property of a formation fluid.

FIG. 6 is a flow chart for a method 60 for estimating a property of a downhole fluid. Block 61 calls for conveying a carrier through a borehole penetrating the earth. Block 62 calls for extracting a sample of the downhole fluid using a formation tester disposed at (i.e., in or on) the carrier. Block 63 calls for depositing the sample in a probe cell having a window. Block 64 calls for illuminating the sample through the window with light photons using a light source. Block 65 calls for receiving light photons through the window that have interacted with the downhole fluid and generating a signal indicative of an amount of the received light photons using a photodetector disposed at (i.e., in or on) the carrier. The photodetector includes an optical cavity that includes or is made up of a semiconductor. The semiconductor has a difference between a valence energy band and a conduction energy band for electrons that is greater than the energy of each of the received light photons. Block 66 calls for estimating the property using a processor that receives the signal.

It can be appreciated that the downhole tool 10 provides several advantages. One advantage is that the photodetector 19 may be used to detect light photons in the near-infrared range with no dark current or significantly reduced dark current as compared to conventional photodetectors. Another advantage is that a filter for filtering light to allow only a certain wavelength to be detected is not required because the optical cavity can provide the filtering function. Yet another advantage is that the disclosed photodetector is small enough that a plurality of photodetectors may be deployed within the limited confines of a downhole tool due to borehole spatial constraints. Yet another advantage is that the plurality of disclosed photodetectors may be fabricated into a single semiconductor chip using semiconductor fabrication techniques to reduce fabrication cost and further reduce size enabling multiple photodetector chips to be used in a single downhole tool to measure multiple fluid properties.

In support of the teachings herein, various analysis components may be used, including a digital and/or an analog system. For example, the downhole electronics 11 or the computer processing system 12 may include digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling component, heating component, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

The term "carrier" as used herein means any device, device component, combination of devices, media and/or member that may be used to convey, house, support or otherwise facilitate the use of another device, device component, combination of devices, media and/or member. Other exemplary non-limiting carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The terms "first," "second" and the like do not denote a particular order, but are used to distinguish different elements.

While one or more embodiments have been shown and described, modifications and substitutions may be made thereto without departing from the spirit and scope of the invention. Accordingly, it is to be understood that the present invention has been described by way of illustrations and not limitation.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for estimating a property of a downhole fluid, the apparatus comprising:
   a carrier configured to be conveyed through a borehole penetrating the earth;
   a fluid extraction device disposed at the carrier and configured to extract a sample of the downhole fluid;
   a probe cell comprising a window and configured to receive the sample;
   a light source configured to illuminate the sample through the window with light photons; and
   a photodetector disposed at the carrier and configured to receive light photons through the window that have interacted with the downhole fluid and generate a signal indicative of an amount of the received light photons, wherein the photodetector comprises an optical cavity comprising a semiconductor having a difference between a valence energy band and a conduction energy band for electrons that is greater than the energy of each of the received light photons, and wherein the photodetector comprising the optical cavity is configured to operate in a downhole environment at least at 200° C.;
   wherein the signal is indicative of the property.

2. The apparatus according to claim 1, further comprising a processor configured to receive the signal and to estimate the property using the signal.

3. The apparatus according to claim 1, wherein the difference is not greater than two times the energy of each of the received light photons.

4. The apparatus according to claim 1, wherein the optical cavity is a photonic crystal.

5. The apparatus according to claim 4, wherein the photonic crystal comprises a Q that is greater than 100,000.

6. The apparatus according to claim 1, wherein the photodetector comprises a first electrode and a second electrode in contact with the optical cavity and configured to conduct electrons in the conduction energy band in a circuit in order to generate the signal.

7. The apparatus according to claim 1, wherein the semiconductor comprises silicon.

8. The apparatus according to claim 1, the apparatus further comprising a current meter coupled to the first and second electrodes and configured to measure electrical current generated by the photodetector.

9. The apparatus according to claim 1, wherein the photodetector is configured to receive the light photons that are transmitted through the sample.

10. The apparatus according to claim 1, wherein the photodetector is configured to receive the light photons that are reflected by the sample.

11. The apparatus according to claim 1, wherein the photodetector comprises a plurality of photodetectors and the optical cavity in each photodetector has a resonant frequency that is different from the resonant frequency of the other photodetectors in the plurality.

12. The apparatus according to claim 11, wherein the resonant frequency of each optical cavity is the same as a light photon frequency of a chemical element of interest in the formation fluid.

13. The apparatus according to claim 11, wherein the plurality of photodetectors is fabricated on a single semiconductor substrate.

14. The apparatus according to claim 11, wherein the optical cavities of the plurality of photodetectors are in a series with an inlet port of one photodetector in the plurality receiving photons from an outlet port of another photodetector in the plurality.

15. The apparatus according to claim 1, wherein the light source is configured to operate at least at 200° C.

16. The apparatus according to claim 15, wherein the photodetector is configured to detect photons in the near-infrared range.

17. The apparatus according to claim 1, wherein the property is a chemical element in the downhole fluid.

18. The apparatus according to claim 1, wherein the downhole fluid is a formation fluid and the fluid extraction device is configured to extract a sample of the fluid from a formation in the earth.

19. The apparatus according to claim 1, wherein the carrier comprises a wireline, a slickline, a drill string or coiled tubing.

20. A method for estimating a property of a downhole fluid, the method comprising:
   conveying a carrier through a borehole penetrating the earth;
   extracting a sample of the downhole fluid using a fluid extraction device disposed at the carrier;
   depositing the sample in a probe cell having a window;
   illuminating the sample through the window with light photons using a light source disposed at the carrier;
   receiving light photons through the window that have interacted with the downhole fluid and generating a signal indicative of an amount of the received light photons using a photodetector disposed at the carrier, the photodetector comprising an optical cavity that comprises a semiconductor having a difference between a valence energy band and a conduction energy band for electrons that is greater than the energy of each of the received light photons, wherein the photodetector comprising the optical cavity is configured to operate in a downhole environment at least at 200° C.; and
   estimating the property using a processor that receives the signal.

21. The method according to claim 20, wherein estimating comprises comparing the received signal to a reference.

\* \* \* \* \*